US012605990B2

(12) United States Patent
Brauer

(10) Patent No.: US 12,605,990 B2
(45) Date of Patent: Apr. 21, 2026

(54) AIR PURIFICATION AND FILTRATION SYSTEM USING UV LIGHT

(71) Applicant: JOYSON SAFETY SYSTEMS ACQUISITION LLC, Auburn Hills, MI (US)

(72) Inventor: Salvatore Brauer, Bloomfield Hills, MI (US)

(73) Assignee: JOYSON SAFETY SYSTEMS ACQUISITION LLC, Auburn Hills, MI (US)

( * ) Notice: Subject to any disclaimer, the term of this patent is extended or adjusted under 35 U.S.C. 154(b) by 854 days.

(21) Appl. No.: 17/491,462

(22) Filed: Sep. 30, 2021

(65) Prior Publication Data

US 2022/0097491 A1 Mar. 31, 2022

Related U.S. Application Data

(60) Provisional application No. 63/085,757, filed on Sep. 30, 2020.

(51) Int. Cl.
| | |
|---|---|
| *A61L 9/20* | (2006.01) |
| *B60H 3/00* | (2006.01) |
| *B60H 3/06* | (2006.01) |

(52) U.S. Cl.
CPC .............. *B60H 3/0078* (2013.01); *A61L 9/20* (2013.01); *B60H 3/0608* (2013.01); *A61L 2209/14* (2013.01); *A61L 2209/16* (2013.01)

(58) Field of Classification Search
CPC ....... B60H 3/0078; B60H 3/0608; A61L 9/20; A61L 2209/14; A61L 2209/16; Y02A 50/2351
USPC .............................. 422/172, 186.03; 454/69
See application file for complete search history.

(56) References Cited

U.S. PATENT DOCUMENTS

| | | | |
|---|---|---|---|
| 6,787,782 | B1 | 9/2004 | Krosney et al. |
| 6,991,532 | B2 | 1/2006 | Goldsmith |
| 7,658,891 | B1* | 2/2010 | Barnes .................... C01B 13/11 |
| | | | 128/205.28 |
| 2015/0360544 | A1* | 12/2015 | Fruehsorger ............ B03C 3/017 |
| | | | 96/19 |
| 2016/0271289 | A1 | 9/2016 | Duffy |
| 2018/0319256 | A1* | 11/2018 | Stahl .................. B01D 46/4245 |

* cited by examiner

*Primary Examiner* — Christine T Mui
(74) *Attorney, Agent, or Firm* — Meunier Carlin & Curfman LLC

(57) ABSTRACT

A system for controlling air quality in a vehicle cabin includes at least one mechanical filtering device receiving unfiltered air and collecting particulate matter from the unfiltered air. Air flow downstream from the mechanical filtering device is a first filtered air flow. At least one ultraviolet (UV) light source is positioned within the vehicle between the at least one mechanical filtering device and the vehicle cabin, wherein the UV light source directs UV light into the first filtered air flow.

12 Claims, 6 Drawing Sheets

100

AIR PURIFICATION AND FILTRATION SYSTEM USING UV LIGHT

CROSS REFERENCE TO RELATED APPLICATIONS

This application claims priority to and incorporates by reference U.S. Provisional Patent Application Ser. No. 63/085,757, filed on Sep. 30, 2020, and entitled Air Purification and Filtration System Using UV Light.

TECHNICAL FIELD

This disclosure relates to improving air quality within the cabin of a vehicle with ultraviolet light.

BACKGROUND

Much like the engine filter, the air cabin filter keeps dust, dirt, pollen, bacteria, and exhaust from entering the HVAC system of the vehicle. On top of that it also keeps larger objects such as bugs, leaves, and other debris from entering the vehicle keeping the cabin clean. As illustrated in prior art FIG. 1, however, these cabin air filters, over time, will degrade in performance. When these filters collect moisture over time they will start to grow and house microbes, bacteria, and mold. UV light, used in traditional HVAC systems in homes has been proven to reduce the risks of mold, bacteria, and microbes. They are also able to remove VOCs (Volatile Organic Compounds), such as acetone and formaldehyde.

SUMMARY

A system for controlling air quality in a vehicle cabin includes at least one mechanical filtering device receiving unfiltered air and collecting particulate matter from the unfiltered air. Air flow downstream from the mechanical filtering device is a first filtered air flow. At least one ultraviolet (UV) light source is positioned within the vehicle between the at least one mechanical filtering device and the vehicle cabin, wherein the UV light source directs UV light into the first filtered air flow.

DETAILED DESCRIPTION

Embodiments of this disclosure utilize ultraviolet (UV) light sources installed within, or at least proximately to, air conduits of vehicle cabin air systems to purify the air content within the vehicle cabin. As used herein, the term vehicle has its broadest plain meaning, including but not limited to automobiles, trucks, airplanes, and any other machinery in which an occupant is positioned and is subject to air quality therein. UV light sources may be positioned directly within air conduits or may be positioned on or sufficiently near an air source or air conduit to direct UV light toward at least a portion of air flow within a vehicle cabin air system. In some embodiments, a traditional mechanical cabin air filter and a UV light source may be connected to each other or be an integral single unit. The embodiments herein also encompass installations in which the UV light travels through ultraviolet light transmissive structures to have an effect on air flow within the vehicle.

Figure 2:
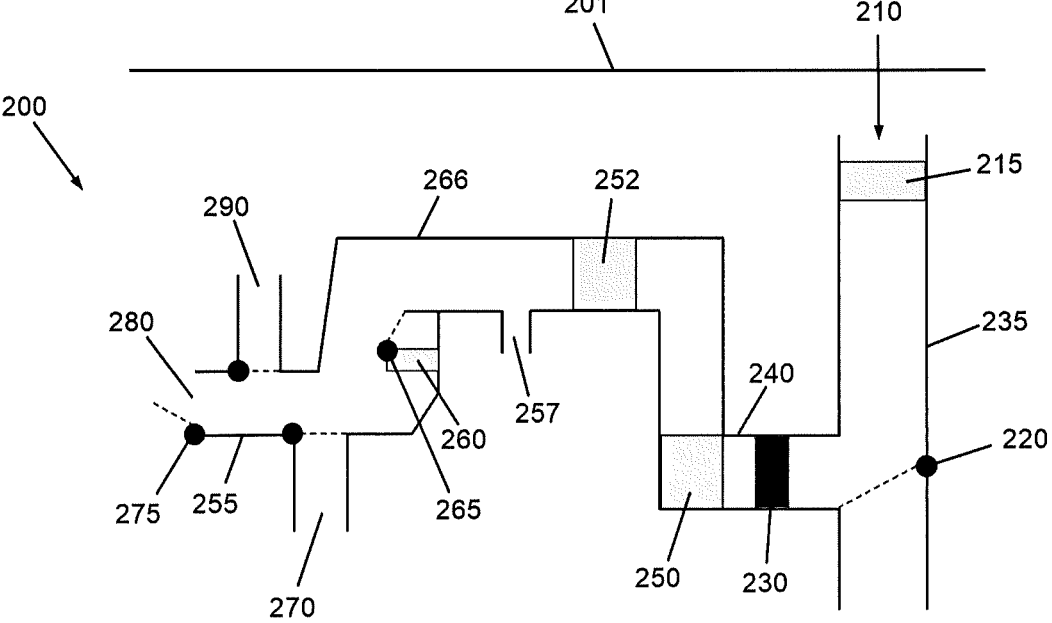
FIG. 2 is a schematic illustration of a cabin air flow system having an ultraviolet light source installed therein with air intake from outside the vehicle cabin.
Figure 3:
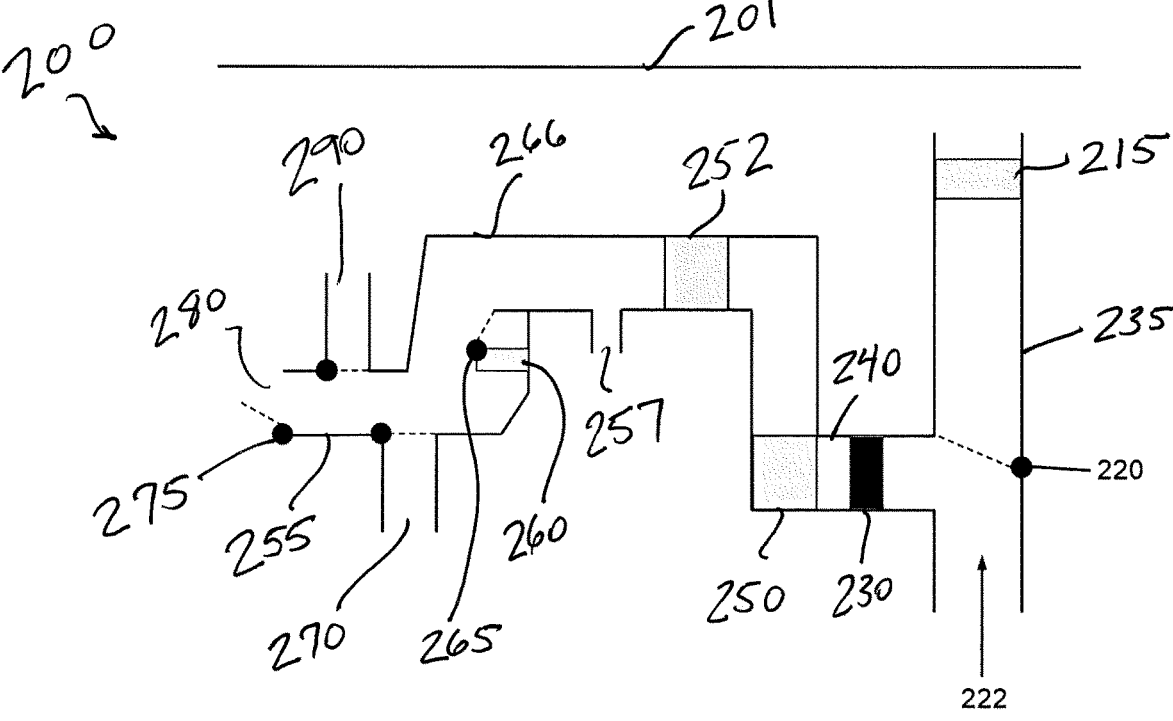
FIG. 3 is a schematic illustration of a cabin air flow system having an ultraviolet light source installed therein with air intake from inside the vehicle cabin.

As shown in the figures, a vehicle cabin air system 200, 300, 400 and 500 may include numerous configurations. One example providing context to this disclosure is illustrated in FIG. 2 with a front of a vehicle (i.e., areas proximate a front windshield 201) providing fresh outside air 210 into the vehicle cabin via previously configured first, second, third, and fourth conduits 235, 240, 255, 266 for air control. The vehicle cabin air system includes typical air handling components including, but not limited to, a mechanical cabin air filter 215 that physically traps contaminants, a recirculation flap 220 (shown in FIG. 2 as including a movable section (i.e., the dotted line) controlling a recirculation mode that is optionally selectable by a vehicle occupant for disallowing (as shown) or allowing incoming cabin air 222 into the first conduit 235). FIG. 3 illustrates an embodiment in which the recirculation flap 220 is closed, allowing the incoming cabin air 222 into the air system 200. In some embodiments, the air system 200, 300, 400 may include a heater and associated blower 250, an evaporator core 252, an evaporator drain 257, a heater core 260, optional blend door 265 for heated air, floor vent conduits 270, variously selectable mode doors 275, main vent conduits 280, and defrost vent conduits 290. Flaps and doors in the figures include movable sections shown in the dotted lines to open and close the flaps and doors for different ways to configure the air systems.

As ride sharing becomes more prevalent and robo-taxis are being developed, these vehicles will have passengers cycling through at a constant rate. Some of these passengers have the potential to be carrying mold, bacteria, viruses . . . . etc. that will completely bypass the air filter. Outside environmental factors can also contaminate air inside the vehicle and its air handling system as well.

This disclosure shows creating a UV light filter where cabin air is continuously being pulled through will help mitigate the passing of these contaminates from one passenger to the next creating a safe and healthy vehicle experience. Outside air contaminated with pollen and mold may also be a concern for health and well-being inside the vehicle. This proposed system will help break down and eliminate those contaminates to create a better ride for the driver and passengers.

Figure 1:
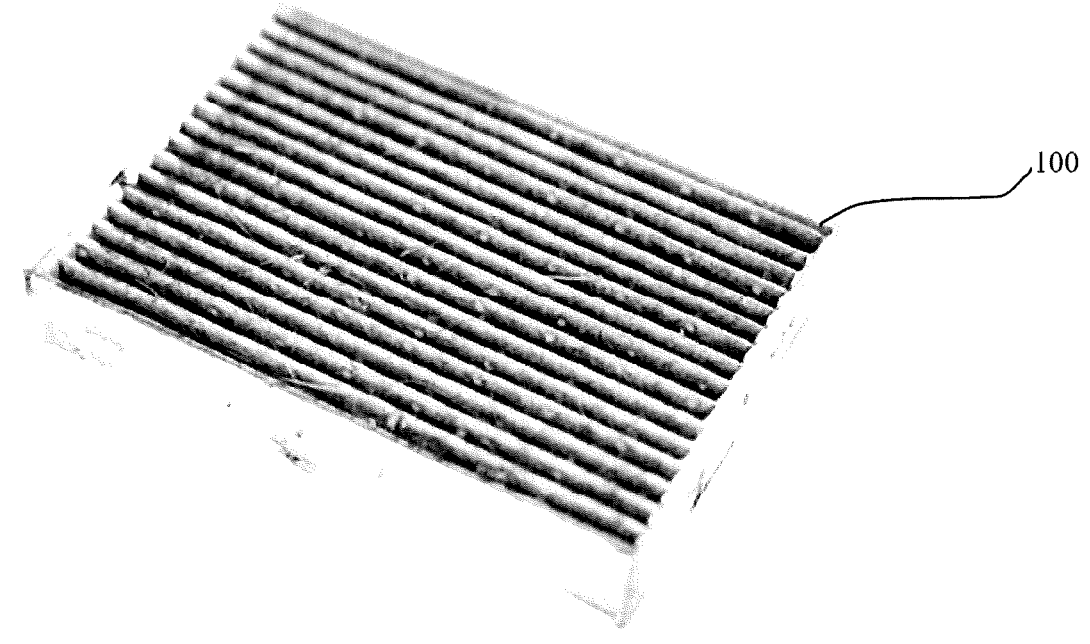
FIG. 1 is a PRIOR ART illustration of a standard air filter subject to prior use in a vehicle.

Along with the current filtration system including standard cabin air filters 100 as illustrated in FIG. 1, this disclosure incorporates at least one UV light source into the air conduits in a vehicle. The UV light source may be a permanent fixture within the vehicle cabin air system or it may be a modular UV light assembly with replaceable filter system components that provide the UV light. As noted above, one non-limiting embodiment of this disclosure is useful to decrease the number of microbes and bacteria transmitted from air sources (outside air, fans, and the like) into the vehicle cabin and into the passenger's body.

Considering FIG. 2-3, embodiments of this disclosure include positioning a UV light source 230 within an air conduit. In one non limiting example, the air conduit encompassing the UV light source is a heater blower feed conduit 240, and the UV light source is oriented to direct UV light into the air flow regardless of the position of the recirculation flap 220 (i.e. the air flow source is either the fresh outside air 210 (FIG. 2) or the cabin air 222 (FIG. 3)). As shown in FIGS. 2 and 3, other optional positions for a UV light source 230 may be sections of the air handling system other than the heater blower feeder conduit 240. Air flow traversing any of the first, second, third and fourth conduits 235, 240, 255, 266 may be subject to the purification effect of UV light directed therein prior to traversing the rest of the system. This is necessary given that the recirculation flap 220 may be in a recirculation position that blocks outside air 210 (FIG. 3) FIG. 3).

Figure 4:
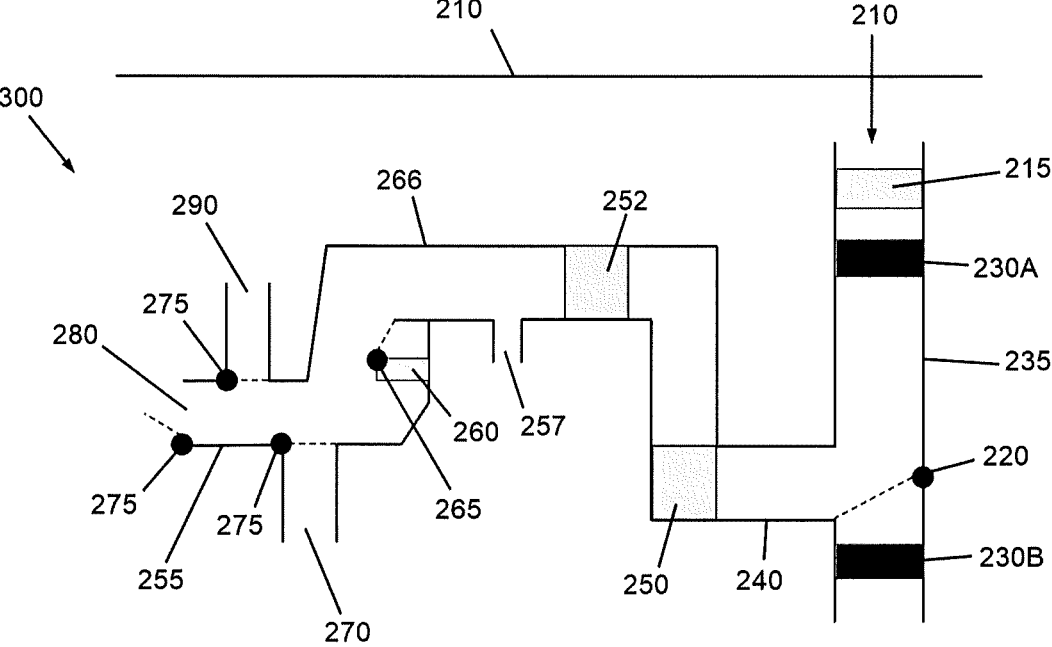
FIG. 4 is a schematic illustration of a cabin air flow system having a plurality of ultraviolet light sources installed therein with air intake from outside the vehicle cabin.
Figure 5:
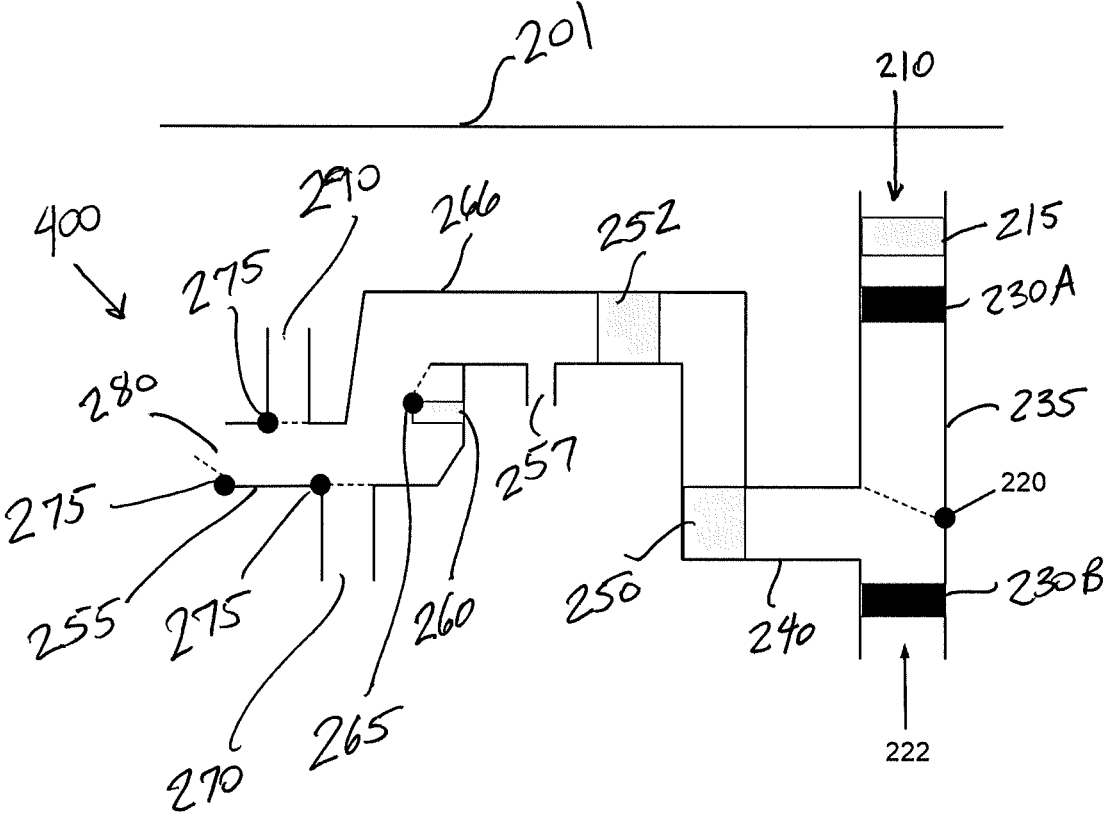
FIG. 5 is a schematic illustration of a cabin air flow system having a plurality of ultraviolet light sources installed therein with air intake from inside the vehicle cabin.
Figure 6:
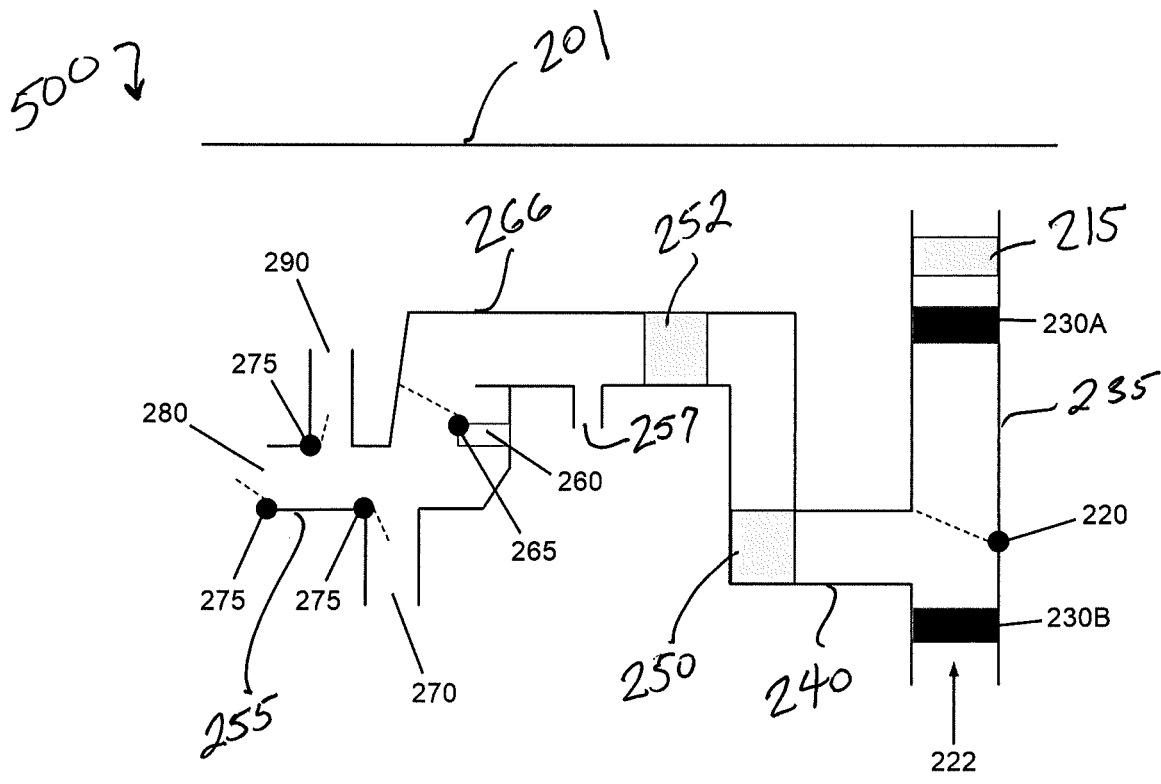
FIG. 6 is a schematic illustration of a cabin air flow system having a plurality of ultraviolet light sources installed therein with a plurality of flaps and doors in different positions.

In regard to FIG. 4, embodiments herein may include a plurality of UV light sources 230A, 230B at respective locations in vehicle cabin air systems. In one non-limiting embodiment, a respective UV light source 230A may be paired with a mechanical cabin air filter 215 to purify incoming air sources as disclosed herein. A separate UV light source 230B may be positioned in a cabin air conduit 235, such as a section receiving air flow during periods where the recirculation option is on, and incoming air is taken into the vehicle cabin air system entirely from within the cabin, as shown in FIG. 5. FIG. 4 illustrates an example embodiment in which UV light sources 230A, 230B are positioned on opposite sides of the recirculation flap 220 which controls the optional recirculation mode in the vehicle. Numerous other positions are likewise available within modern vehicle cabin air systems, such as opening and closing a heating air flap 265 in FIG. 6.

Vehicle cabin air systems described herein may be controlled via a computer having a processor and memory storing and implementing computerized algorithms that depend upon sensors in a vehicle cabin to monitor air quality. The computerized algorithms may be implemented with computer processors and computerized memory for electronic air quality control.

Although the present disclosure has been described in detail with reference to particular arrangements and configurations, these example configurations and arrangements may be changed significantly without departing from the scope of the present disclosure. Moreover, although network devices are illustrated with reference to particular elements and operations that facilitate the communication process, these elements, and operations may be replaced by any suitable architecture or process that achieves the intended functionality of network device.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. The structures shown in the accompanying figures are susceptible to 3-D modeling and can be described relative to vertical, longitudinal, and lateral axes established with reference to neighboring components as necessary.

Note that in this Specification, references to various features (e.g., elements, structures, modules, components, steps, operations, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments. Note also that an "application" as used herein this Specification, can be inclusive of an executable file comprising instructions that can be understood and processed on a computer, and may further include library modules loaded during execution, object files, system files, hardware logic, software logic, or any other executable modules.

In example implementations, at least some portions of the activities may be implemented in software provisioned on a networking device. In some embodiments, one or more of these features may be implemented in computer hardware, provided external to these elements, or consolidated in any appropriate manner to achieve the intended functionality. The various network elements may include software (or reciprocating software) that can coordinate in order to achieve the operations as outlined herein. In still other embodiments, these elements may include any suitable algorithms, hardware, software, components, modules, interfaces, or objects that facilitate the operations thereof.

Furthermore, computer systems described and shown herein (and/or their associated structures) may also include suitable interfaces for receiving, transmitting, and/or otherwise communicating data or information in a network environment. Additionally, some of the processors and memory elements associated with the various nodes may be removed, or otherwise consolidated such that single processor and a single memory element are responsible for certain activities. In a general sense, the arrangements depicted in the Figures may be more logical in their representations, whereas a physical architecture may include various permutations, combinations, and/or hybrids of these elements. It is imperative to note that countless possible design configurations can be used to achieve the operational objectives outlined here. Accordingly, the associated infrastructure has a myriad of substitute arrangements, design choices, device possibilities, hardware configurations, software implementations, equipment options, etc.

In some of example embodiments, one or more memory elements (e.g., memory) can store data used for the operations described herein. This includes the memory being able to store instructions (e.g., software, logic, code, etc.) in non-transitory media, such that the instructions are executed to carry out the activities described in this Specification. A processor can execute any type of computer readable instructions associated with the data to achieve the operations detailed herein in this Specification. In one example, processors (e.g., processor) could transform an element or an article (e.g., data) from one state or thing to another state or thing. In another example, the activities outlined herein may be implemented with fixed logic or programmable logic (e.g., software/computer instructions executed by a processor) and the elements identified herein could be some type of a programmable processor, programmable digital logic (e.g., a field programmable gate array (FPGA), an erasable programmable read only memory (EPROM), an electrically erasable programmable read only memory (EEPROM)), an ASIC that includes digital logic, software, code, electronic instructions, flash memory, optical disks, CD-ROMs, DVD ROMs, magnetic or optical cards, other types of machinereadable mediums suitable for storing electronic instructions, or any suitable combination thereof.

These devices may further keep information in any suitable type of non-transitory storage medium (e.g., random access memory (RAM), read only memory (ROM), field programmable gate array (FPGA), erasable programmable read only memory (EPROM), electrically erasable programmable ROM (EEPROM), etc.), software, hardware, or in any other suitable component, device, element, or object where appropriate and based on particular needs. Any of the memory items discussed herein should be construed as being encompassed within the broad term 'memory element.' Similarly, any of the potential processing elements, modules, and machines described in this Specification should be construed as being encompassed within the broad term "processor."

These and other aspects of this disclosure are set forth in the claims below.

The invention claimed is:

1. A system for controlling air quality in a vehicle cabin, the system comprising:

at least one mechanical filtering device receiving unfiltered air from outside the vehicle cabin into an outside air inlet conduit and collecting particulate matter from the unfiltered air to create a first filtered air flow;

a recirculation flap positioned in the outside air inlet conduit receiving the first filtered air flow, said recirculation flap being movable to allow and disallow the first filtered air flow into a blower feed conduit directing air flow into the vehicle cabin;

an ultraviolet (UV) light source positioned within the blower feed conduit between the at least one mechanical filtering device and the vehicle cabin, wherein the UV light source directs UV light into the air flow within the blower feed conduit regardless of a position of the recirculation flap allowing or disallowing the first filtered air flow.

2. A system according to claim 1, wherein the mechanical filtering device is positioned in the outside air inlet conduit.

3. A system according to claim 2, further comprising a heater core positioned in the blower feed conduit.

4. The system according to claim 1, wherein the UV light source is a modular UV light assembly.

5. The system according to claim 1, wherein the recirculation flap is movable to a recirculation position that blocks outside air or cabin air from the blower feed conduit.

6. A system for controlling air quality in a vehicle cabin, the system comprising:

at least one mechanical filtering device receiving unfiltered air from outside the vehicle cabin into an outside air inlet conduit and collecting particulate matter from the unfiltered air to create a first filtered air flow;

a recirculation flap positioned in the outside air inlet conduit receiving the first filtered air flow, said recirculation flap being movable to allow and disallow the first filtered air flow into a second conduit;

an ultraviolet (UV) light source positioned within the outside air inlet conduit, wherein the UV light source directs UV light into the first filtered air flow; and an additional UV light source positioned in the second conduit, wherein the additional UV light source directs UV light into a cabin air flow during a recirculation mode in which the recirculation flap is positioned to disallow the first filtered air flow into the second conduit.

7. The system according to claim 6, wherein the UV light source is a modular UV light assembly.

8. A system for controlling air quality in a vehicle cabin, the system comprising:

at least one mechanical filtering device receiving unfiltered air from outside the vehicle cabin into an outside air inlet conduit and collecting particulate matter from the unfiltered air to create a first filtered air flow;

a recirculation flap positioned in the outside air inlet conduit receiving the first filtered air flow, said recirculation flap being movable to allow and disallow the first filtered air flow into a second conduit;

an ultraviolet (UV) light source positioned within the outside air inlet conduit, wherein the UV light source directs UV light into the first filtered air flow; and an additional UV light source positioned on an opposite side of the recirculation flap in another conduit;

wherein the additional UV light source directs UV light into a cabin air flow during a recirculation mode in which the recirculation flap is positioned to disallow the first filtered air flow into the another conduit connected to the outside air inlet conduit.

9. The system of claim 8, wherein the additional UV light source directs UV light into a cabin air flow during a recirculation mode in which the recirculation flap is positioned to disallow the first filtered air flow into the second conduit.

10. The system of claim 8, wherein the additional UV light source directs UV light into the first filtered air flow.

11. The system according to claim 8, wherein at least one of the UV light source or the additional UV light source is a modular UV light assembly.

12. The system according to claim 8, wherein the recirculation flap is movable to a recirculation position that blocks outside air or cabin air from the second conduit.

* * * * *